(12) United States Patent
Gillies et al.

(10) Patent No.: US 9,511,203 B2
(45) Date of Patent: Dec. 6, 2016

(54) SYSTEM AND METHOD TO TRIGGER BREATHING RESPONSE FOR THE REDUCTION OF ASSOCIATED ANXIETY

(75) Inventors: Murray Fulton Gillies, Eindhoven (NL); Tim Johannes Willem Tijs, Eindhoven (NL); Jürgen Vogt, Eindhoven (NL); Constance Jeanne Elizabeth Saalberg-Seppen, Vessem (NL); Gijs Antonius Franciscus Van Elswijk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 189 days.

(21) Appl. No.: 14/111,614

(22) PCT Filed: Apr. 2, 2012

(86) PCT No.: PCT/IB2012/051593
§ 371 (c)(1),
(2), (4) Date: Oct. 14, 2013

(87) PCT Pub. No.: WO2012/140538
PCT Pub. Date: Oct. 18, 2012

(65) Prior Publication Data
US 2014/0046121 A1 Feb. 13, 2014

(30) Foreign Application Priority Data
Apr. 14, 2011 (EP) .................................... 11162367

(51) Int. Cl.
*A61M 21/02* (2006.01)
*A61B 5/00* (2006.01)
(Continued)

(52) U.S. Cl.
CPC ............ *A61M 21/02* (2013.01); *A61B 5/0205* (2013.01); *A61B 5/4836* (2013.01); *A61B 5/743* (2013.01);
(Continued)

(58) Field of Classification Search
CPC .................... A61M 21/02; A61M 2021/0022; A61M 2021/005; A61M 2021/0088; A61M 2230/005; A61M 2230/06; A61M 2230/42; A61M 2230/65; A63B 23/185; A63B 2230/425; A63B 71/0622; A63B 2071/0636; A63B 2230/062; A63B 2230/655; A61B 5/0205; A61B 5/4836; A61B 5/743; A61B 5/7455
See application file for complete search history.

(56) References Cited

U.S. PATENT DOCUMENTS 6,305,943 B1 10/2001 Pougatchev et al.
8,465,289 B2 6/2013 Kameyama et al.
(Continued)

FOREIGN PATENT DOCUMENTS

EP 0872255 10/1998
WO WO2007105127 9/2007
(Continued)

*Primary Examiner* — Christine H Matthews
*Assistant Examiner* — Joshua D Lannu (57) ABSTRACT

A system and a method include a display configured to display video and/or still images, and an image source that is in communication with the display and configured to allow content of the image source to be displayed on the display. Further, the system and method include a physiological information gatherer configured to obtain a current physiological information of a patient when the patient is positioned to see the video and/or still image on the display. A processor is configured to receive the current physiological information from the physiological information gatherer, and the processor, being in communication with the image
(Continued)

source, is further configured to transmit to the display the current physiological information and a target breathing rate.

18 Claims, 3 Drawing Sheets

(51) Int. Cl.
  *A63B 23/18* (2006.01)
  *A63B 71/06* (2006.01)
  *A61B 5/0205* (2006.01)
  *A61M 21/00* (2006.01)
  *A61B 5/08* (2006.01)

(52) U.S. Cl.
  CPC ........... *A61B 5/7455* (2013.01); *A63B 23/185* (2013.01); *A63B 71/0622* (2013.01); *A61B 5/0816* (2013.01); *A61M 2021/005* (2013.01); *A61M 2021/0022* (2013.01); *A61M 2021/0088* (2013.01); *A61M 2230/005* (2013.01); *A61M 2230/06* (2013.01); *A61M 2230/42* (2013.01); *A61M 2230/65* (2013.01); *A63B 2071/0636* (2013.01); *A63B 2230/062* (2013.01); *A63B 2230/425* (2013.01); *A63B 2230/655* (2013.01)

(56) References Cited

U.S. PATENT DOCUMENTS

| | | |
|---|---|---|
| 2002/0007105 A1 | 1/2002 | Prabhu et al. |
| 2004/0224822 A1* | 11/2004 | Verheem .......................... 482/8 |
| 2005/0124906 A1* | 6/2005 | Childre et al. ................ 600/529 |
| 2007/0244384 A1 | 10/2007 | Gore |
| 2010/0113865 A1* | 5/2010 | Chung et al. .................. 600/27 |
| 2010/0231483 A1 | 9/2010 | Bazih et al. |
| 2011/0183305 A1* | 7/2011 | Orbach .................... A61B 5/16 434/236 |

FOREIGN PATENT DOCUMENTS

| | | |
|---|---|---|
| WO | WO2009097548 | 8/2009 |
| WO | WO2009133517 | 11/2009 |

* cited by examiner

SYSTEM AND METHOD TO TRIGGER BREATHING RESPONSE FOR THE REDUCTION OF ASSOCIATED ANXIETY

CROSS-REFERENCE TO PRIOR APPLICATIONS

This application is the U.S. National Phase application under 35 U.S.C. §371 of International Application Serial No. PCT/IB2012/051593, filed on Apr. 2, 2012, which claims the benefit of European Application Serial No. 11162367.4, filed on Apr. 14, 2011. These applications are hereby incorporated by reference herein.

FIELD OF THE INVENTION

The present invention relates to a system and method for use in connection with anxiety. Further the present invention relates to a system and method for use in connection with breathing exercises.

BACKGROUND OF THE INVENTION

Anxiety in individuals is often triggered by associations that the person has with an object or activity. This response is often well-founded and has been developed during human evolution as a way of creating alertness in human beings for potential threats. A high level of alertness in the presence of real threats ultimately leads to an improved chance of survival.

It is, however, often the case that an individual has an anxiety association which may not be justified, i.e. there is only a perceived threat rather than an actual threat. This is often referred to as an anxiety disorder.

Anxiety disorder (AD) is a general term covering several forms of abnormal and pathological reactions to fear. AD and the subdivisions thereof were only recognized by psychiatry at the very end of the 19th century but are actually relatively common, with some reports estimating that as many as 18% of Americans may be affected by one or more ADs. Treatment options include pharmaceutical therapy and psychotherapy.

Looking at a physiological level then situations that are not perceived as threatening result in a balance of the sympathetic, i.e. fight or flight, and parasympathetic, i.e. "rest and digest", branches of the human autonomic nervous system. In the case of anxiousness then this balance shifts toward sympathetic dominance.

The inventor of the present invention has appreciated that a system for treating anxiety of a patient without requiring the presence of a therapist is of benefit, and has in consequence devised the present invention.

SUMMARY OF THE INVENTION

It would be advantageous to achieve a system and method for reducing anxiety in individuals. In general, the invention preferably seeks to mitigate, alleviate or eliminate one or more of the above mentioned disadvantages singly or in any combination. In particular, it may be seen as an object of the present invention to provide a method and system that solves the above mentioned problems, or other problems, of the prior art.

To better address one or more of these concerns, in a first aspect of the invention a system is presented that comprises a display unit configured for displaying video and/or still images, an image source in communication with the display unit so as to allow content of the image source to be displayed on the display unit, a physiological information gathering unit configured to obtain current physiological information of a patient when the patient is positioned to see the video and/or still image on the display unit, and a processor for receiving current physiological information from the physiological information gathering unit, the processor being in communication with the image source, the processor being configured to transmit to the display unit a combination of the current physiological information and a target breathing rate.

One technical problem resides in that the patient needs to be taught to take a specific number of breaths per minute when exposed to a certain image or movie illustrative of a situation that triggers anxiety in the patient. By simultaneously showing an image or movie and graphically showing the patient what his or her current breathing rate is and simultaneously showing to the patient what the breathing rate should be, the patient is made aware of how much the breathing should be changed.

As will be discussed inhalation triggers the sympathetic nervous system and the flight or fight reaction. In a preferred embodiment a positive image is shown, e.g. picture of nature, in this period. The image that normally triggers anxiety is shown in the exhalation period when the parasympathetic, relax reflex, is triggered.

It is an advantage of the present invention that the physiological information gathering unit may be constituted by a breathing rate monitor unit and/or heart rate monitor unit and/or an electrodermal unit. A system may comprise several different actual implementations of the physiological information gathering unit, so as to allow an operator to choose which type is most effective in a given situation. Some patients may experience discomfort using an electrodermal unit etc.

In an embodiment the physiological information regarding the patient is obtained using a photoplethysmograph, or other non-invasive device of obtaining information regarding the patients breathing rate and/or heart rate. The non-invasive or non-contact device may be more efficient for patients suffering from anxiety for medical devices such as CT-scanners and the like as the physical contact with the skin when using a device being mounted to the patient may distract the patient further.

Advantageously the physiological information includes specification of exhale rate and/or inhale rate and/or inhale/exhale ratio. As mentioned above, inhalation triggers the sympathetic nervous system and the flight or fight reaction. Advantageously a positive image is shown, e.g. picture of nature, in this period. The image that normally triggers anxiety is shown in the exhalation period when the parasympathetic, relax reflex, is triggered. The images that normally triggers anxiety could be images of confined spaces, images of insects such as spiders, images or video of medical equipment such as CT- or MR-scanners or other equipment where the patient is placed inside the equipment, such a video sequence could be displayed over a number of exhalation periods, where a small piece of the video sequence is displayed each period. The video could for instance include a camera nearing the equipment and ending in the place where the patient is to be positioned.

Advantageously the system may further comprise a light source. The light source is preferably directed so as to expose the patient to light. The light source is configured to flicker at a first frequency, the light source flicker being controlled by the processing unit so that the light is flickered at the first frequency when an image from a first group is displayed. An embodiment comprising such a light source makes use of the fact that repetitive visual stimulation, e.g. the flicker, at a frequency larger than 30 Hz can entrain gamma brainwaves within an individual.

Advantageously the images and/or videos in the image source may be ranked according to an anxiety provoking level value. This allows the method to comprise the processor being configured to display images and/or video with a certain anxiety provoking level value and the processor determining if the current physiological information of the patient viewing the images and/or video is below a threshold, and provided the current physiological information is below the threshold the processor displaying a next image having a higher certain anxiety provoking level value.

Advantageously the image source comprises images of words that the patient is to read out loud. This is contemplated to be advantageous for people with speech impediments such as stuttering.

Advantageously the current physiological information comprises exhalation period information and the processor is configured to display a word at the beginning of the exhalation period. This may be advantageous when treating stuttering.

Advantageously the physiological information gathering unit is a breathing rate monitor unit and/or heart rate monitor unit and the method comprises displaying the current breathing rate monitor and/or heart rate on the display unit, alternatively the method comprises providing a tactile device configured to provide feedback regarding the physiological information to the patient. The feedback enhances the patients training of breathing rate and thereby the patient's body faster association with positive feelings when exposed to anxiety inducing objects and/or situations.

A second aspect of the present invention relates to a method for using a system, the system comprising a display unit configured for displaying video and/or still images, an image source in communication with the display unit so as to allow content of the image source to be displayed on the display unit, a physiological information gathering unit configured to obtain current physiological information of a patient when the patient is positioned to see the video and/or still image on the display unit, and a processor for receiving current physiological information from the physiological information gathering unit, the processor being in communication with the image source, the processor being configured to transmit to the display unit a combination of the current physiological information and a target breathing rate, the method comprises displaying an image on the display unit, obtaining current physiological information via the physiological information gathering unit, and displaying the current physiological information together with a desired physiological information level on the display unit.

Advantageously the physiological information includes specification of exhale rate and/or inhale rate, and wherein the image source comprises images and/or videos in two categories, a first category wherein the images or videos comprises an object triggering a anxiety reflex in a patient, and a second category triggering relax reflex in a patient, the method comprising displaying images in two time periods, a first period where images from the first category is displayed, and a second period where images from the second category is displayed, the first period being correlated to the exhalation period and the second period being correlated to the inhalation period. Displaying two different images or video sequences in the different time periods is advantageous in that the patient then associates the images or video to an appropriate physical state, i.e. parasympathetic and sympathetic reflex as described in the present specification.

Advantageously the system further comprising a light source, the light source being configured to flicker at a first frequency, the light source flicker being controlled by the processing unit, the method may then comprise flickering the light at the first frequency when an image from a first group is displayed. The first frequency may advantageously be larger than 30 Hertz.

An embodiment of the system including a light device takes advantage of the fact that repetitive visual stimulation, e.g. the flicker, at a frequency larger than 30 Hz can entrain gamma brainwaves in an individual. Gamma band activity in the brain is associated with cognitive performance. It is therefore contemplated to repeating the positive-negative imagery cycle but upon exposing the positive image the image, a light source directed at the patient, is flickered.

As mentioned above, the images and/or videos in the image source may be ranked according to an anxiety provoking level value. This allow the method to comprise the processor being configured to display images and/or video with a certain anxiety provoking level value and the processor determining if the current physiological information of the patient viewing the images and/or video is below a threshold, and provided the current physiological information is below the threshold the processor displaying a next image having a higher certain anxiety provoking level value.

Advantageously the image source comprises images of words that the patient is to read out loud, the method comprises displaying a word. This is contemplated to be advantageous for people with speech impediments such as stuttering. For these individuals a word which has to be read is shown in the background at the time of exhalation. The individual is asked to pace his breathing and read the displayed word. When the patient follows these directions is contemplated to alleviate the patients stuttering.

Advantageously the current physiological information comprises exhalation period information and the method comprises displaying a word at the beginning of the exhalation period. It may be preferable that the individual does not use the whole exhalation period for pronunciation. If this is the case then the word can be displayed for a fraction of exhalation. A data storage may comprise indication of a time period that is to be used for each word and this is read by the system and used to position the word in the exhalation period.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

In some situations it is not possible for an individual to deal with the association that causes anxiety and, in the case where the anxiety is severe this may hamper the person in everyday life. Examples of this are phobias such as fear of insects or animals, fear of dentist, fear of flying, fear for medical procedures such as an MR- or CT-scan. The anxiety for the machine is most probably often related to the confinement in a narrow tunnel combined with a high volume noise; something, which from an evolutionary point of view, is understandably perceived as threatening.

Therapy is a commonly accepted and effective way of dealing with anxiety-related issues. There are many therapeutic ways and techniques of trying to weaken the association that people have developed between objects or experiences and the perceived threat. The most common method is the supply of information which often rationalizes the perceived threat and reduces the level of anxiety.

Another method is to introduce the individual to the threat in a controlled and dosed manner and slowly increase this dose whereby allowing the person to become accustomed to the threat. This is known as Cognitive Behavioral Therapy (CBT) and has been proven to be highly effective in randomized controlled trials. These trials, together with other evidence, have led to the UK's National Institute for Health and Clinical Excellence recommending CBT for use within England and Wales. CBT is based on the theory that the fear response has been classically conditioned and that avoidance negatively reinforces and maintains that fear. Fear can be expressed by patients verbally and physiologically, e.g. disturbances of normal heart rate and breathing rate patterns. CBT is typically done by, and believed to be most effective in the presence of a human therapist.

Another method of reducing anxiety association is to encourage the person to try and consciously control their physiological response when presented with the threat. This often includes elements of visualization, e.g., think of a distractor image when presented with the threat, or breathing exercises. The latter technique is used to restore the sympathetic-parasympathetic balance in the autonomic nervous system. "Slow breathing" is one breathing technique to do so; prolonged exhalation is another, based on the knowledge that inhalation triggers sympathetic activity and exhalation triggers parasympathetic activity.

One of the current drawbacks of therapy is that it requires (in many cases) the presence of a therapist, which is fairly costly.

The present invention provides a system and method that alleviates or overcome some of these issues.

Figure 1:
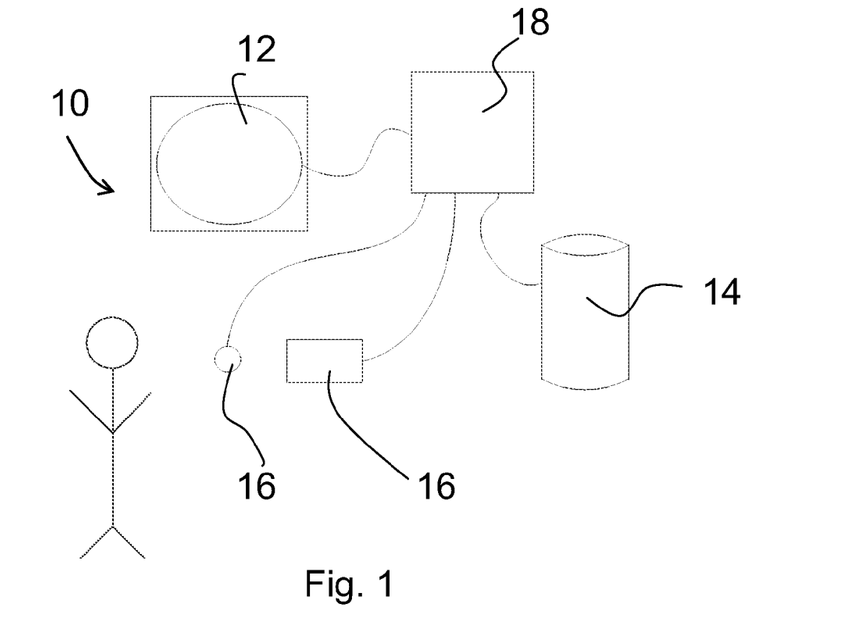
FIG. 1 is a schematic illustration of a system according to the present invention and a person.

FIG. 1 illustrates a system 10 comprising a display unit 12 configured for displaying video and/or still images. The system 10 comprises an image source 14 in communication with the display unit so as to allow content of the image source to be displayed on the display unit. The system 10 comprises a physiological information gathering unit 16 configured to obtain current physiological information of a patient when the patient is positioned to see the video and/or still image on the display unit. The system 10 comprises a processor 18 for receiving current physiological information from the physiological information gathering unit, the processor being in communication with the image source, the processor being configured to transmit to the display unit a combination of the current physiological information and a target breathing rate.

Figure 3:
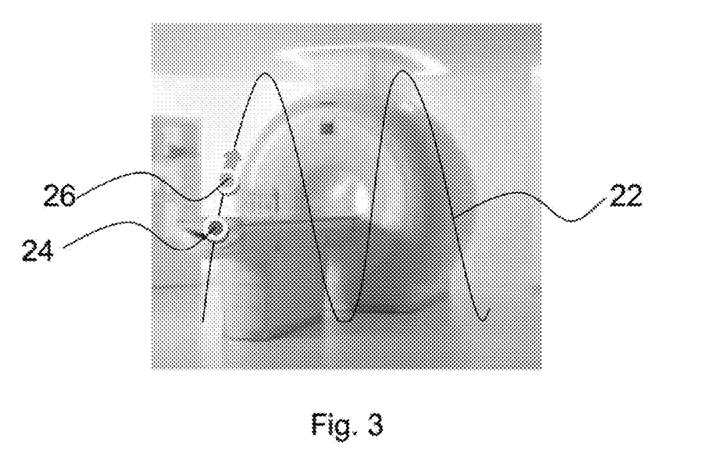
FIG. 3 is a schematic illustration of a screen view.

A session may be defined. The session may be composed of a period where one image is shown on the display unit and the breathing pattern is monitored and displayed. Such an image is illustrated in FIG. 3. A sine, or cosine, wave 22 is illustrated with one dot 24 illustrating the current breathing rate of the patient and one dot 26 illustrating the target breathing rate of e.g. 6 breaths per minute. As will be discussed later a session may be composed of a number of periods where different images or videos are displayed. Further, one or more breaks may be introduced in the session. Still further an operator may pause or interrupt the session if the patient feels too much discomfort. Other options are discussed below.

In a presently preferred embodiment the physiological information gathering unit is constituted by a breathing rate monitor unit and/or heart rate monitor unit and/or an electrodermal unit. A system may comprise several different actual implementations of the physiological information gathering unit, so as to allow an operator to choose which type is most effective in a given situation. Some patients may experience discomfort using an electrodermal unit etc.

The present invention provides a system where the breathing pattern of a patient is measured and used to give visual feedback on the breathing rate. The breathing pattern is then preferably adapted to be approximately 6 breaths per minute, a rate which has been shown to induce relaxation. This concept is known as paced breathing.

The system and method according to the present invention allows display of images of the anxiety inducing subject at the same time as the breathing exercise is performed. After sufficient practice of the breathing exercises this will not only create an association of being relaxed when exposed to images of the threat but will also create an association between performing slow breathing or, prolonged, exhalation upon exposure to the object. This association is then exploited when the person is really exposed to the perceived threat and reacts by lowering the breathing rate. This can be either a conscious or subconscious reaction to the threat imagery The general embodiment includes a projection or TV screen, i.e. a display unit of some sort, a device for measuring the breathing rate of the individual situated in front of the screen, a computer unit that records the breathing rate and couples this to the content being shown on the screen in such a way that the patient becomes aware of his breathing rate while at the same time being exposed to imagery considered threatening in light of the phobia of the patient. The breathing rate is measured either by a breathing belt or preferably a camera based solution or another device for obtaining physiological information.

In an embodiment the physiological information regarding the patient is obtained using a photoplethysmograph, or other non-invasive device of obtaining information regarding the patients breathing rate and/or heart rate. The non-invasive or non-contact device may be more efficient for patients suffering from anxiety for medical devices such as CT-scanners and the like as the physical contact with the skin when using a device being mounted to the patient may distract the patient further.

Advantageously the physiological information includes specification of exhale rate and/or inhale rate and/or inhale/exhale ratio. As mentioned above inhalation triggers the sympathetic nervous system and the flight or fight reaction. Advantageously a positive image is shown, e.g. picture of nature, in this period. The image that normally triggers anxiety is shown in the exhalation period when the parasympathetic, relax reflex, is triggered. The images that normally trigger anxiety could be images of confined spaces, images of insects such as spiders, images or video of medical equipment such as CT- or MR-scanners or other equipment where the patient is placed inside the equipment, such a video sequence could be displayed over a number of exhalation periods, where a small piece of the video sequence is displayed each period. The video could for instance include a camera nearing the equipment and ending in the place where the patient is to be positioned.

By monitoring the physiological data the current state of the patient may be determined. E.g. it can be determined when the patient is in a relatively relaxed state or agitated or anxious state. The images or video displayed may be chosen depending on the current state of the patient.

In an embodiment when the individual appears to be comfortable with the imagery then a content algorithm can start to move the transition so that the negative, threat image is shown also for a fraction of the inhalation period. By gradually increasing the time that the negative image is shown then the patient is slowly exposed to the threat image for the entire breathing cycle.

Figure 2:
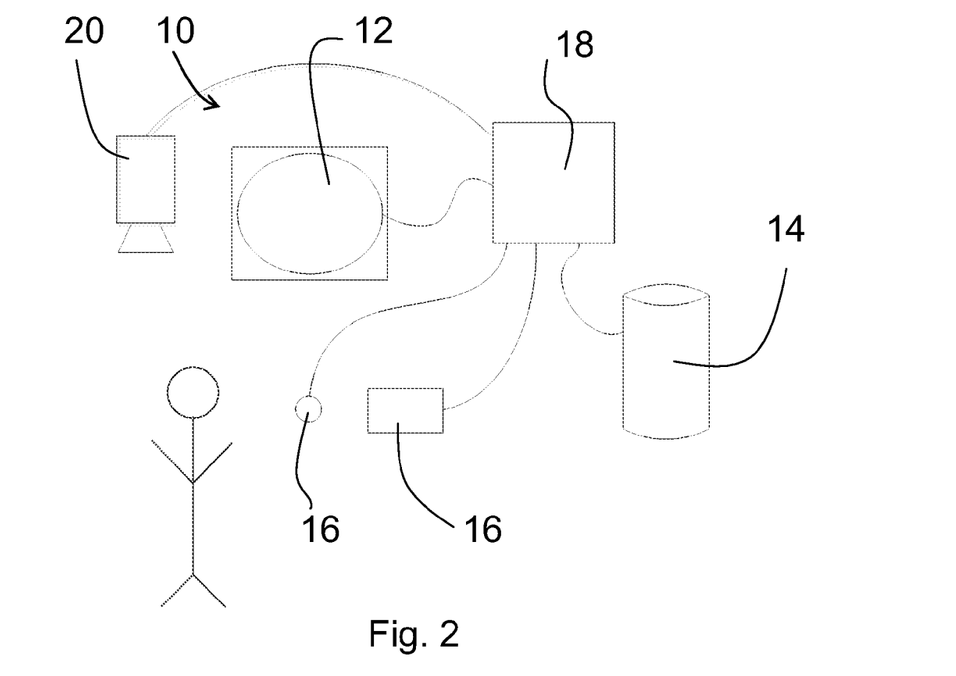
FIG. 2 is a schematic illustration of a second system according to the present invention and a person.

Advantageously the system 10 may further comprise a light source 20, as illustrated in FIG. 2. The light source 20 is preferably directed so as to expose the patient to light. The light source is configured to flicker at a first frequency, the light source flicker being controlled by the processing unit so that the light is flickered at the first frequency when an image from a first group is displayed. An embodiment comprising such a light source makes use of the fact that repetitive visual stimulation, e.g. the flicker, at a frequency larger than 30 Hz can entrain gamma brainwaves within an individual. Thus the first frequency is preferably larger than 30 Hz. Gamma band activity in the brain is associated with cognitive performance. It is therefore contemplated that repeating the positive-negative imagery cycle but upon exposing the positive image the image, or a light source near-by, is flickered presents an advantage. When the negative image is shown the flickering light is turned off. As the individual starts to become more comfortable with the negative image then the flicker is either slowly reduced to zero or may even be used to bias towards the negative image. This visual stimulation usually involves luminance changes but hue, saturation or phase changes may also be used to entrain brain activity.

Advantageously images and/or videos in the image source are ranked according to an anxiety provoking level value. The rank may then be used to determine which images are to be shown in a given session. Prior sessions may be recorded and the choice of which rank of images to be shown may be based on this record. The processor is then configured to display images and/or video with a certain anxiety provoking level value and the processor being configured to determine if the current physiological information of the patient viewing the images and/or video is below a threshold, and provided the current physiological information is below the threshold the processor being configured to display images having a higher certain anxiety provoking level value. Further, a sequence of images having a specific rank pattern may be determined, e.g. a rising rank level through a session over a period of time.

In such an embodiment the exposure intensity, i.e. how extreme the imagery is, or the rate of negative imagery is adaptive to a, physiological, arousal measurement, such as electrodermal or cardiac activity. Thus, the system will increase the intensity of exposure to the stress stimulus only if the physiological arousal levels fall within specified limits. In this way the subject can slowly adapt to the stressor.

Advantageously the image source comprises images of words that the patient is to read out loud. Such an embodiment is specifically targeted for people with speech impediments such as stuttering. For these individuals then a word which has to be read is shown in the background at the time of exhalation. The individual is asked to pace his breathing and read the displayed word. The words to be displayed can be held in an initialization file.

It may be preferable that the individual does not use the whole exhalation period for pronunciation. If this is the case then the word can be displayed for a fraction of exhalation. The initialization file may contain a time period that is to be used for each word and this is read by the system and used to position the word in the exhalation period. Further, the current physiological information comprises exhalation period information and the processor is configured to display a word at the beginning of the exhalation period.

Figure 6:
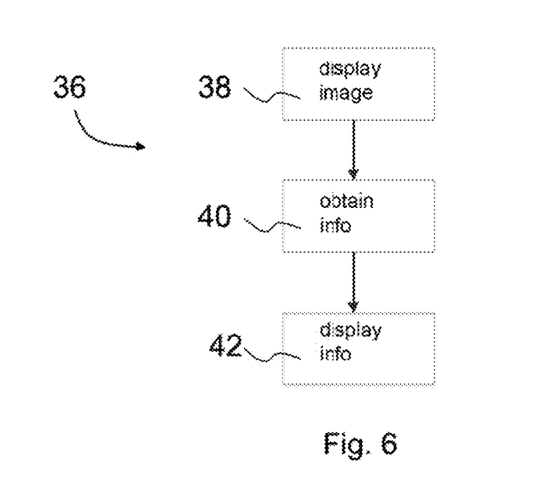
FIG. 6 is a schematic illustration of a method according to the present invention.

FIG. 6 illustrates steps of a method 36 for using a system. The system is preferably of the type discussed above. The system comprising a display unit configured for displaying video and/or still images, an image source in communication with the display unit so as to allow content of the image source to be displayed on the display unit, a physiological information gathering unit configured to obtain current physiological information of a patient when the patient is positioned to see the video and/or still image on the display unit, a processor for receiving current physiological information from the physiological information gathering unit, the processor being in communication with the image source, the processor being configured to transmit to the display unit a combination of the current physiological information and a target breathing rate. The method 36 comprises the steps of displaying 38 an image on the display unit, obtaining 40 current physiological information via the physiological information gathering unit, and displaying 42 the current physiological information together with a desired physiological information level on the display unit. The steps are not necessarily listed in sequence. There may be preceding, intermediate and subsequent steps.

Advantageously the physiological information gathering unit is a breathing rate monitor unit and/or heart rate monitor unit and the method comprises displaying the current breathing rate monitor and/or heart rate on the display unit, alternatively the method comprises providing a tactile device configured to provide feedback regarding the physiological information to the patient. The feedback enhances the patients training of breathing rate and thereby the patient's body faster association with positive feelings when exposed to anxiety inducing objects and/or situations.

Further it may be advantageous to monitor the breathing or heart rate, or the variance thereof, response to anxiety inducing images as a way of monitoring the therapy aimed at de-coupling the anxiety response from the object.

Figure 4:
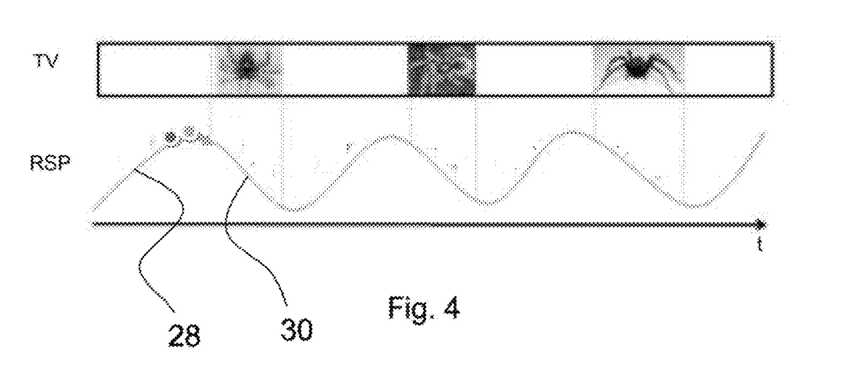
FIG. 4 is a schematic illustration of an embodiment of the present invention.

Advantageously the breathing data (RSP) includes specification of exhale rate and/or inhale rate, and wherein the image source comprises images and/or videos in two categories, a first category wherein the images or videos comprises an object triggering a anxiety reflex in a patient, and a second category triggering relax reflex in a patient, the method comprising displaying images in two time periods, a first period where images from the first category is displayed, and a second period where images from the second category is displayed, the first period being correlated to the exhalation period and the second period being correlated to the inhalation period. This is schematically illustrated in FIG. 4, where in the sympathetic period 28 one type of image is displayed, and in the parasympathetic period 30 another type of image is displayed. In the period 28 a non-anxiety provoking image is displayed. In the period 30 an anxiety provoking image is displayed.

Advantageously the system further comprising a light source, the light source being configured to flicker at a first frequency, the light source flicker being controlled by the processing unit, the method may then comprise flickering the light at the first frequency when an image from a first group is displayed. The first frequency may advantageously be larger than 30 Hertz, An embodiment with such a light device takes advantage of the fact that repetitive visual stimulation, e.g. the flicker, at a frequency larger than 30 Hz can entrain gamma brainwaves in an individual. Gamma band activity in the brain is associated with cognitive performance. It is therefore suggested that repeating the positive-negative imagery cycle but upon exposing the positive image the image, or a light source directed at the patient, is flickered. When the negative image is shown the flickering is turned off. As the individual starts to become more comfortable with the negative image then the flicker is either slowly reduced to zero or may even be used to bias towards the negative image. This visual stimulation usually involves luminance changes but hue, saturation or phase changes may also be used to entrain brain activity.

Figure 5:
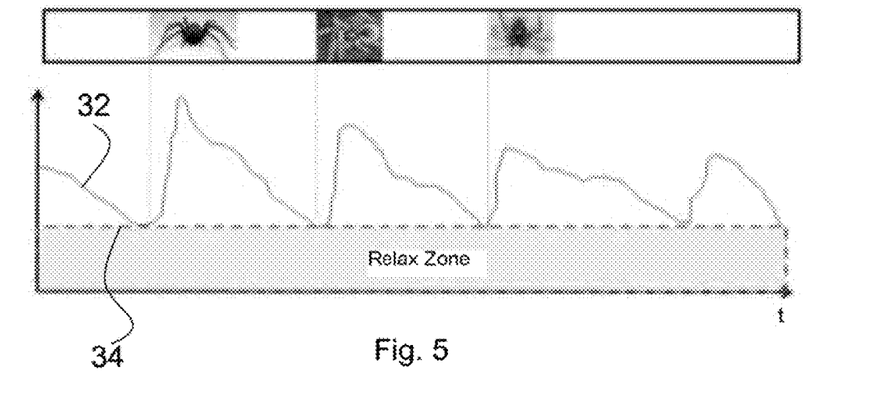
FIG. 5 is a schematic illustration of graph.

As mentioned above, the images and/or videos in the image source may be ranked according to an anxiety provoking level value. This allow the method to comprise the processor being configured to display images and/or video with a certain anxiety provoking level value and the processor determining if the current physiological information of the patient viewing the images and/or video is below a threshold, and provided the current physiological information is below the threshold the processor displaying a next image having a higher certain anxiety provoking level value. Such an embodiment is illustrated in FIG. 5 where the breathing rate, or ratio, is indicated by the graph 32 and the threshold is indicated by the line 34.

In this case the exposure intensity, i.e. how extreme the imagery is, or the rate of negative imagery is adaptive to a, physiological, arousal measurement, such as electrodermal, breathing rate or cardiac activity. Thus, the system will increase the intensity of exposure to the stress stimulus only if the physiological arousal levels fall within specified limits. In this way the subject can slowly adapt to the stressor illustrated in the image or video.

Advantageously the image source comprises images of words that the patient is to read out loud, the method comprises displaying a word. This is meant specifically for people with speech impediments such as stuttering. For these individuals a word which has to be read is shown in the background at the time of exhalation. The individual is asked to pace his breathing and read the displayed word. The words to be displayed can be held in an initialization file or database or the like.

It may be preferable that the individual does not use the whole exhalation period for pronunciation. If this is the case then the word can be displayed for a fraction of exhalation. The initialization file may contain a time period that is to be used for each word and this is read by the system and used to position the word in the exhalation period.

Advantageously the current physiological information comprises exhalation period information and the method comprises displaying a word at the beginning of the exhalation period.

Advantageously the anxiety inducing images are specifically medical devices or procedures that the patient has a phobia for, such as images of CT-scanners, MR-scanners, surgery procedures, needles or similar situations or devices.

The images and/or video displayed may be 2D or 3D. The 3D effect may enhance the patient's perception of the object which triggers the anxiety compared to 2D.

The features mentioned in relation to the system apply equally to the method and vice versa.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCE NUMERALS 10 system
12 display unit
14 image source
16 physiological information gathering unit
18 processor
20 light source
22 wave
24 dot
26 dot
28 sympathetic period
30 parasympathetic period
32 graph
34 threshold line
36 method
38 the step of displaying
40 the step of obtaining
42 the step of displaying

The invention claimed is:
1. A system comprising:
a display configured to display images and/or videos;
an image source configured to be in communication with the display, the image source comprising a content, the content being the images and/or videos, and the image source being further configured to allow the content to be displayed on the display;
a physiological information gatherer configured to measure a current physiological information of a patient when the patient is positioned to see the images and/or videos on the display; and a processor configured to receive the measured current physiological information from the physiological information gatherer, the processor being further configured to be in communication with the image source, and the processor being further configured to transmit to the display the measured current physiological information and a target breathing rate for display on the display,
wherein the images and/or videos in the image source are ranked according to an anxiety provoking level value, wherein the anxiety provoking level value is a degree of anxiety of the patient caused by the images and/or videos in the image source,
wherein the processor is configured to display on the display a first image and/or video with a first anxiety provoking level value,
wherein the processor is configured to determine when the measured current physiological information of the patient viewing the images and/or videos is below a threshold,
wherein when the measured current physiological information is below the threshold, the processor is configured to display on the display a second image and/or video having a second anxiety provoking level value higher than the first anxiety provoking level value of the first image and/or video, and
wherein the processor is configured to select the first and second images and/or videos of the images and/or videos in the image source and output the selected first and second images and/or videos to the display for display based on the measured current physiological information of the patient and the anxiety provoking level value of the images and/or videos in the image source that are ranked.

2. The system according to claim 1, wherein the physiological information gatherer comprises at least one of a breathing rate monitor, a heart rate monitor and an electrodermal monitor.

3. The system according to claim 1, wherein the measured current physiological information of the patient is configured to be measured using a photoplethysmograph.

4. The system according to claim 1, wherein the measured current physiological information displayed on the display comprises a specification of at least one of an exhale rate, an inhale rate and an inhale-exhale ratio.

5. The system according to claim 1, further comprising a light source, the light source being configured to flicker at a frequency, and the light source being configured to be controlled by the processor, wherein the light source is further configured to flicker at the frequency when a first group of the images and/or videos are displayed.

6. The system according to claim 5, wherein the light source is further configured to turn off when a second group of the images and/or videos are displayed, the second group of the images and/or videos having anxiety provoking level values different from the first group.

7. The system according to claim 1, wherein the content of the image source comprises images of words configured to be displayed on the display, and wherein the patient is prompted to read out loud the images of words displayed.

8. The system according to claim 7, wherein the measured current physiological information comprises information of an exhalation period and the display is further configured to display a word of the images of words at a beginning of the exhalation period, the word of the images of words having the anxiety provoking level value.

9. The system according to claim 1, wherein the measured current physiological information of the patient is configured to be obtained using at least one of a non-invasive device and a non-contact device of obtaining information regarding a breathing rate and/or a heart rate of the patient.

10. A method comprising acts of:
displaying images and/or videos on a display;
allowing a content of an image source to be displayed on the display by configuring the image source to be in communication with the display, the content comprising the images and/or videos;
measuring via a physiological information gatherer a measured current physiological information of a patient when the patient is positioned to see the images and/or videos on the display;
receiving the measured current physiological information from the physiological information gatherer by a processor, the processor being in communication with the image source;
transmitting by the processor to the display the measured current physiological information and a target breathing rate for display on the display:
displaying on the display the measured current physiological information together with a desired physiological information level;
ranking the images and/or videos in the image source according to an anxiety provoking level value, wherein the anxiety provoking level value is a degree of anxiety of the patient caused by the images and/or videos in the image source;
displaying on the display a first image and/or video with a first anxiety provoking level value via the processor;
determining by the processor when the measured current physiological information of the patient viewing the images and/or video is below a threshold;
displaying on the display via the processor a second image having a second anxiety provoking level value higher than the first anxiety provoking level when the measured current physiological information is below the threshold; and
selecting by the processor the first and second images and/or videos of the images and/or videos of the image source and outputting the selected first and second images and/or videos to the display for display based on the measured current physiological information of the patient and the anxiety provoking level value of the images and/or videos in the image source that are ranked.

11. The method according to claim 10, wherein the physiological information gatherer comprises at least one of a breathing rate monitor and a heart rate monitor, and wherein the method further comprises one of an act of displaying a current breathing rate and/or a current heart rate on the display; and an act of providing a tactile device configured to provide feedback regarding the measured current physiological information to the patient.

12. The method according to claim 10, wherein the measured current physiological information comprises a specification of an exhale rate in an exhalation period and/or an inhale rate in an inhalation period, wherein the image source comprises the images and/or videos in a first category and a second category, wherein the images and/or videos of the first category comprise an object triggering an anxiety reflex in the patient, and wherein the images and/or videos of the second category comprise a further object triggering a relax reflex in the patient, and wherein the method further comprises an act of displaying the images and/or videos in a first time period and a second time period, the first time period is where the images and/or videos from the first category are displayed, and the second time period is where the images and/or videos from the second category are displayed, the first time period being correlated to the exhalation period and the second time period being correlated to the inhalation period.

13. The method according to claim 10, further comprising an act of flickering a light source at a frequency, the flickering act being controlled by the processor, and wherein the flickering act further comprises an act of flickering the light source at the frequency when a first group of the images and/or videos are displayed.

14. The method according to claim 10, further comprising an act of displaying a word, wherein the content of the image source further comprises images of words, and wherein the patient is prompted to read the word out loud.

15. The method according to claim 14, further comprising an act of displaying the word at a beginning of an exhalation period, wherein the measured current physiological information comprises information of the exhalation period.

16. A system comprising:
a display configured to display images and/or videos;
an image source configured to be in communication with the display, the image source comprising a content, the content being the images and/or videos, and the image source being further configured to allow the content to be displayed on the display;
a physiological information gatherer configured to measure a current physiological information of a patient when the patient is positioned to see the images and/or videos on the display; and
a processor configured to receive the measured current physiological information from the physiological information gatherer, the processor being further configured to be in communication with the image source, and the processor being further configured to transmit to the display the measured current physiological information and a target breathing rate to be displayed on the display,
wherein the images and/or videos in the image source are ranked according to an anxiety provoking level value, wherein the anxiety provoking level value is a degree of anxiety of the patient caused by the images and/or videos in the image source, and
wherein the processor is configured to select images and/or videos from the images and/or videos of the image source and output the selected images and/or videos to the display for display based on the measured current physiological information and anxiety provoking level values of the images and/or videos in the image source that are ranked.

17. The system of claim 16, wherein the processor is configured to display on the display a first image and/or video with a first anxiety provoking level value.

18. A system comprising:
a display configured to display images and/or videos;
an image source configured to be in communication with the display, the image source comprising a content, the content being the images and/or videos, and the image source being further configured to allow the content to be displayed on the display;
a physiological information gatherer configured to measure a current physiological information of a patient when the patient is positioned to see the images and/or videos on the display; and
a processor configured to receive the measured current physiological information from the physiological information gatherer, the processor being further configured to be in communication with the image source, and the processor being further configured to transmit to the display the measured current physiological information and a target breathing rate to be displayed on the display,
wherein the display is further configured to display a first image and/or video with a first anxiety provoking level value,
wherein the processor is further configured to determine when the measured current physiological information of the patient viewing the images and/or videos is below a threshold, and wherein when the measured current physiological information is below the threshold, the processor is configured to display on the display second image and/or video having a second anxiety provoking level value higher than the first anxiety provoking level value of the first image and/or video, and
wherein the processor is configured to select the first and second images and/or videos of the images and/or videos of the image source and output the selected first and second images and/or videos to the display for display based on the measured current physiological information of the patient and an anxiety provoking level value of the images and/or videos in the image source, wherein the anxiety provoking level value is a degree of anxiety of the patient caused by the images and/or videos in the image source.

* * * * *